United States Patent
George et al.

(10) Patent No.: US 6,777,450 B1
(45) Date of Patent: Aug. 17, 2004

(54) WATER-THIN EMULSIONS WITH LOW EMULSIFIER LEVELS

(75) Inventors: Liliana George, Centerport, NY (US); Andrew J. Bevacqua, East Setauket, NY (US); Gheorghe Cioca, Lake Grove, NY (US); Michelle Matathia, Plainview, NY (US); Charles Craig Tadlock, Islip Terrace, NY (US)

(73) Assignee: Color Access, Inc., Melville, NY (US)

( * ) Notice: Subject to any disclaimer, the term of this patent is extended or adjusted under 35 U.S.C. 154(b) by 0 days.

(21) Appl. No.: 09/580,743

(22) Filed: May 26, 2000

(51) Int. Cl.$^7$ .............................. B01F 3/08; A61K 9/113
(52) U.S. Cl. .............................. 516/54; 516/69; 516/70; 516/73; 514/938; 514/943; 435/839; 424/401
(58) Field of Search .............................. 516/54, 69, 73, 516/70; 514/938, 943, 9, 11; 435/839; 424/401

(56) References Cited

U.S. PATENT DOCUMENTS

| | | | |
|---|---|---|---|
| 3,936,391 A | * 2/1976 | Gabby et al. | 516/73 X |
| 4,254,105 A | * 3/1981 | Fukuda | 514/943 X |
| 4,400,295 A | * 8/1983 | Ootsu et al. | 516/69 |
| 4,454,113 A | * 6/1984 | Hemker | 516/73 X |
| 4,784,845 A | * 11/1988 | Desai et al. | 514/938 X |
| 5,178,871 A | * 1/1993 | Thill | 514/938 X |
| 5,264,363 A | * 11/1993 | Carrera et al. | 435/839 X |
| 5,674,509 A | * 10/1997 | Date et al. | 514/938 X |
| 5,976,604 A | * 11/1999 | Kunieda et al. | 516/73 X |
| 5,994,414 A | * 11/1999 | Franco et al. | 514/938 |
| 6,140,375 A | * 10/2000 | Nagahama et al. | 516/73 |

FOREIGN PATENT DOCUMENTS

| | | | |
|---|---|---|---|
| CA | 2188331 | 10/1996 | ........... A23L/1/307 |
| DE | 19846772 | 10/1998 | ............ A61K/7/42 |
| WO | WO 91/01970 | 2/1991 | |
| WO | WO 96/37180 | 11/1996 | |
| WO | WO 97/25971 | * 7/1997 | |
| WO | WO 98/47464 | 10/1998 | |
| WO | 99/62482 | 12/1999 | ............ A61K/7/48 |
| WO | 00/33806 | 6/2000 | ............ A61K/7/48 |

OTHER PUBLICATIONS

Structure, Interfacial Properties and Functional Qualities in Foams and Emulsions of Surfactin, a Lipopeptide from *Bacillus subtilis*—Deleu, et al. XP 008001035 1999.

George, Liliana S., Ph.D., et al., "Versatile and Efficient Emulsification Technology Based on a Non–Conventional Anionic Rheology Modifier", Proceedings—Advanced Technology Conference: Europe 1998, Cosmetics & Toiletries magazine, pps. 38–46 (1998).

* cited by examiner

Primary Examiner—Daniel S. Metzmaier
(74) Attorney, Agent, or Firm—Karen A. Lowney

(57) ABSTRACT

The invention relates to a water-thin emulsion comprising a non-phospholipid, non-ethoxylated pseudoemulsifier system, the system having a chemical composition with at least one hydrophobic moiety and at least one polar moiety, the size, shape and/or planar arrangement of the hydrophobic and polar moieties being asymmetrical with respect to each other. The emulsion of the invention is prepared by high-pressure homogenization of a crude oil and water emulsion containing the pseudoemulsifier. The emulsions require little or no traditional emulsifier to maintain stability, and are particularly useful in the preparation of multiple emulsions.

19 Claims, 2 Drawing Sheets

WATER-THIN EMULSIONS WITH LOW EMULSIFIER LEVELS

FIELD OF THE INVENTION

The invention relates to cosmetic and pharmaceutical formulations. More specifically, the invention relates to cosmetic and pharmaceutical formulations containing low levels of emulsifiers.

BACKGROUND OF THE INVENTION

One of the most common vehicles for cosmetic and pharmaceutical products is the emulsion. Because they are formed by the dispersion of an oil in water, or water in an oil, they provide great versatility in the delivery of different types of active ingredients. A single oil and water formulation can be used to deliver both oil soluble and water soluble active components, thereby giving the formulation a range of potential activity that cannot be matched by a single phase system.

There are of course limitations to an emulsion vehicle, by virtue of its combination of two inherently incompatible phases. First, an emulsion ordinarily will have a certain amount of innate viscosity; while not necessarily a problem per se, the thickness of the emulsion can prevent its use in certain types of products or packaging that require a less viscous texture. In addition, in order to maintain a stable dispersion, it is ordinarily necessary to add to the formulations substantial amounts of emulsion stabilizers and/or emulsifiers. The necessity of addition of these materials not only adds cost to the final product, but also has an effect on the quality of the final product, by affecting the way the emulsion breaks, as well as how it feels on the skin. Added stabilizers can add to the viscosity of the emulsion, and certain emulsifiers can be irritating to the skin of some users.

There have been attempts to overcome some of these difficulties. One common approach is the use of high pressure homogenization techniques, in which a crude emulsion is passed through a high pressure homogenizer to yield a relatively thin emulsion. This technique can contribute to a reduction in the viscosity of the emulsion, and such emulsions have even been stated as being made with relatively low levels of emulsifiers. However, the emulsifiers used in these situations are either of the type that are known to cause irritation, i.e., non-ionic ethoxylated emulsifiers, or amphoteric, lecithin-type (phospholipid) emulsifiers, which, being naturally-occurring products, are rather costly to use. In some cases, these emulsions will still require an addition of emulsion stabilizers to maintain stability over long periods of time. There thus continues to be a need for a water-thin emulsion which employs minimal levels of a non-irritating emulsifier.

SUMMARY OF THE INVENTION

The present invention relates to water-thin emulsions prepared by high pressure homogenization, in the presence of a non-phospholipid, non-ethoxylated "pseudoemulsifier" having a chemical composition comprising at least one hydrophobic moiety, and at least one polar moiety, the size and/or the planar arrangement of the hydrophobic and polar moieties being asymmetrical with respect to each other. Preferably, the pseudoemulsifier contains at least two of one or of both of the types of moieties. Although not ordinarily effective for use alone in maintaining stability of emulsions, the pseudoemulsifiers have been shown to be highly effective in maintaining the stability of these water-thin emulsion, even at very low levels, i.e., less than 1%, and in addition are very mild and non-irritating to the skin. The water-thin emulsions find a variety of uses as a base for both cosmetic and pharmaceutical products. The invention also provides a method for producing a water-thin emulsion, comprising mixing oil and water phases in the presence of the pseudoemulsifier, and subjecting the mixture to high pressure homogenization.

DETAILED DESCRIPTION OF THE INVENTION

The emulsions of the invention have substantially no viscosity, i.e., they exhibit approximately the consistency of water. The admission consistency of the emulsions is primarily due to their processing under high pressure homogenization. In brief, the emulsion is prepared, in accordance with art-recognized techniques, by forming a crude mixture of the oil and water phases, in the presence of the appropriate emulsifier (as defined in more detail below), and passing it through a high pressure homogenizer for a time sufficient to achieve a stable emulsion. The pressure sufficient to achieve the stable emulsion ranges from about 15,000 to about 45,000 psi, or about 1000–3100 bar, preferably about 1300–3000 bar, utilizing one or more passes. Suitable homogenizers for this purpose are commercially available; these include a microfluidizer, Dee Bee 2000 (BEE International) and Cavitator (Five Star International). The preferred emulsion is an oil-in-water emulsion.

Figure 1A:
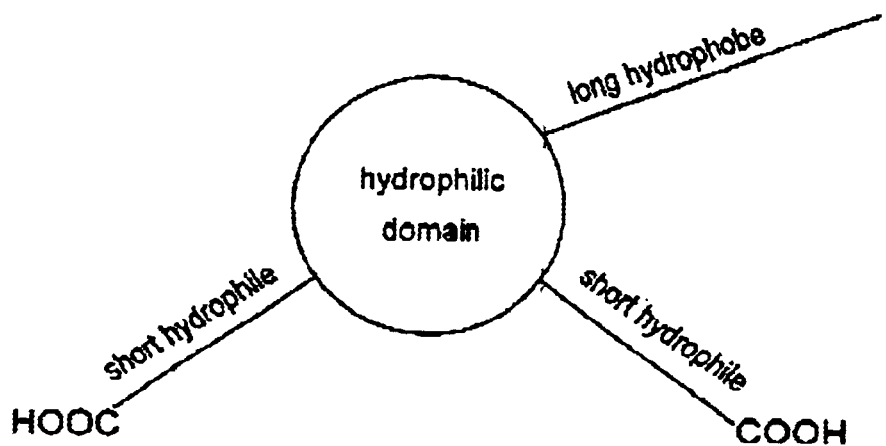
FIGS. 1a and 1b are schematic-illustrations of possible different arrangements of hydrophobic and hydrophilic moieties in the pseudoemulsifiers of the present invention.
Figure 1B:
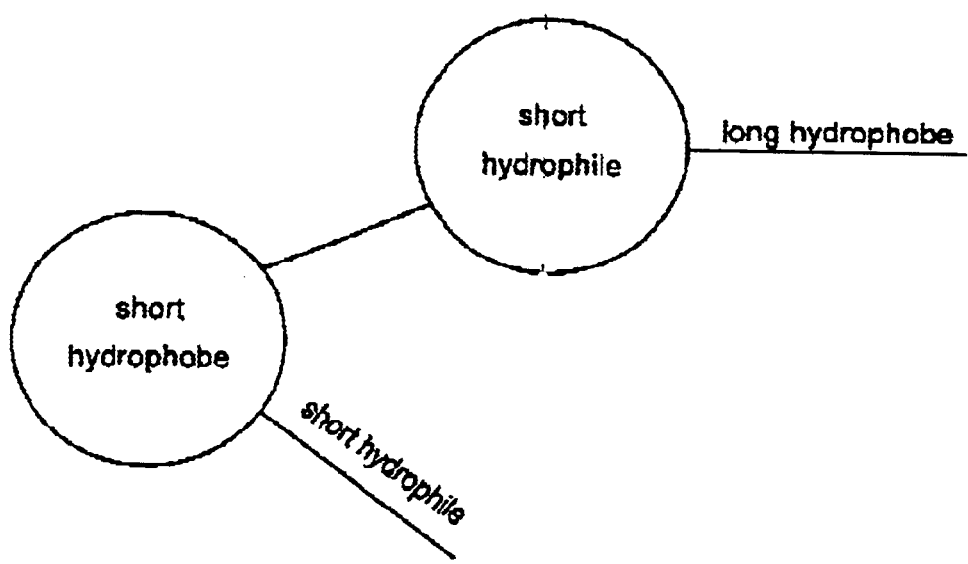

While the homgenization process is important in obtaining the appropriate consistency of the emulsion, this aspect alone is not unique. The water-thin emulsions of the present invention utilize a type of non-ethoxylated, non-phospholipid "pseudoemulsifier", i.e., a compound or compounds that are not traditionally considered or used as emulsifiers, and/or which, when used alone in a traditional emulsion, are ordinarily not capable of stabilizing the emulsion at the very low levels used in the present invention. The type of emulsifier used is a non-ethoxylated, non-phospholipid having a chemical composition containing both hydrophobic moieties and polar (or hydrophilic) moieties, but with an asymmetrical molecular arrangement of the moieties. By "asymmetrical" is meant that the different moieties are of different sizes (e.g., short chain vs. long chain) and/or shapes (e.g., straight chain vs. cyclic), and/or are arranged in different three-dimensional planes within the composition. Preferably, the pseudoemulsifier is a single compound in which there are at least two of either the hydrophilic or hydrophobic moieties. The moieties of a given type may be the same or different, but are preferably different from each other, e.g., a compound will preferably have at least two different hydrophilic moieties, and/or at least two different hydrophobic moieties. Hydrophobic moieties can be any primarily hydrocarbon moiety, including, but not limited to, C1–40 linear or branched, substituted or unsubstituted alkyl, cycloalkyl, alkylene, alkaryl, or aryl groups. The polar or hydrophilic moieties are, for example, hydroxyl, carboxyl, ester, or amide groups, or hydrocarbon moieties that are highly substituted with such polar groups, or combinations thereof. Preferably, the moieties of the same type in a compound are also unequal in size or shape, for example, the hydrophobic moieties can be an alkyl and an aryl group, or two alkyls of different chain length. It is most preferable that the pseudoemulsifier have at least one closed, rigid structure, which can be either hydrophilic or hydrophobic in nature, for example, an aliphatic ring with ether, ester or amide linkages, or an aromatic ring, the rigid structure being anchored by at least one long-chain, i.e., C8–22, straight or branched hydrophobe or hydrophile, and one or two short chain hydrophiles or hydrophobes. Particularly preferred long-chain moieties are C8–22 fatty acid moieties, such as stearate or palmitate. Schematic illustrations of some possible different arrangements of groups in a single compound are shown in FIG. 1. The preferred arrangements provide for a broadly dispersed hydrophilic domain separating the components of the hydrophobic domain. Ordinarily, such molecules will not be readily water-soluble or oil-soluble at room temperature, but will be readily dispersible in either at higher temperatures.

In the case in which the emulsifier does not have a rigid structure per se, it is possible to confer the necessary rigidity by combining the emulsifier with a polymer having dispersed hydrophilic groups along the molecule, to form an emulsifier system. Polymers of this type will hydrogen-bond within the system, thereby creating the structure needed to mimic the desirable structure described above. Examples of useful polymers of this type include sugars, such as disaccharides, e.g., sucrose, lactose, or maltose, and polysaccharides, e.g., cellulose, pectin, xanthan gum, or amylose; or a predominantly hydrophillic peptide or protein, i.e., ones having a preponderance of hydrophilic or polar amino acid residues.

Although it is preferred that the emulsifier components be combined in a single molecule, it is also possible to create a mixture of compounds, having a similar balance of polar and hydrophobic moieties and "asymmetry" as described above, i.e., comprising more than one compound, the compounds used containing a mixture of hydrophobic components and polar or hydrophilic components as described above for the moieties of a single compound, and which mixture will accomplish the same result as the use of the single compound. The combination of compounds should have an overall average HLB value of between 6 and 8. In one embodiment, the components used can incorporate one hydrophilic and one hydrophobic moiety in a single molecule for example, a glycerol ester, such as polyglyceryl-2-isostearate or a sucrose or glucose ester, such as sucrose stearate or sucrose cocoate, in combination with one or more compounds which have hydrophilic or hydrophobic moieties. As with the single compound embodiment, it is preferred that there be at least two hydrophobic moieties or at least two hydrophilic moieties present in the components employed. In the case in which separate compounds are used to contribute the individual hydrophilic and hydrophobic moieties, however, the requisite structure or rigidity will not be present without the addition of a polymer to tie the components together. Therefore, with separate compounds being used, the addition of a polymer with disperse hydrophilic groups is important; the polymer will act, as described above, by forming hydrogen bonds with the other components, forming a cohesive system comparable to the single compound system. When used, in either the single compound or multiple compound system, the polymer is employed in an amount of about 0.1 to about 2%. Although the mixture per se does not necessarily have an innate asymmetry, except perhaps in the different size and/or conformation of the different compounds, the combination in situ in the emulsion will self-assemble asymmetrically.

An example of one embodiment of the single compound structures is a group of anionic emulsifiers of the type that is disclosed in PCT Publication No. WO 91/01970, the contents of which are incorporated herein by reference. One class of compounds are 2-amidocarbonyl-benzoic acid surfactants having the formula (I):

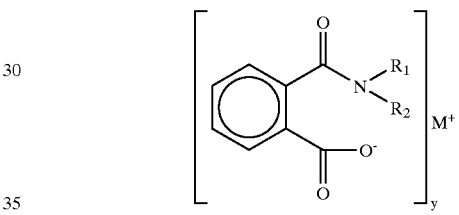

wherein $R_1$ and $R_2$ are independently H or $(CH_2)_nCH_3$, wherein n=8–22, provided that at least one of $R_1$ and $R_2$ is H, wherein $M^+$ is a cation selected from the group consisting of H, Na, K, $NH_4$ and derivatives thereof (for example, basic amino acids), Ba, Ca, Mg, Al, Ti, and Zr, and y is an integer of a value satisfying the valency of $M^+$. Particularly preferred among this class of surfactants is a monovalent salt of stearyl amidobenzoic acid, preferably a sodium salt, also known as RM1. This compound and others of its type are commercially available from Stepan Company, Northfield, Ill. These compounds are known surfactants, which have previously been reported to form stable oil-in-water emulsions when combined with a low HLB emulsifier, or a polymeric emulsifier. However, in the present case, these emulsifiers can be used as the sole emulsifier, at very low levels (i.e., as low as 0.25%) to achieve a stable emulsion; this result is particularly unexpected with an anionic emulsifier alone or at low levels. As can readily be seen from the structure depicted above, these compounds contain two hydrophobic groups, in the presence of the aromatic ring and the long-chain fatty acid side chain, separated by two hydrophilic groups, namely, the carboxylate and amide portions of the molecule.

Figure 2:
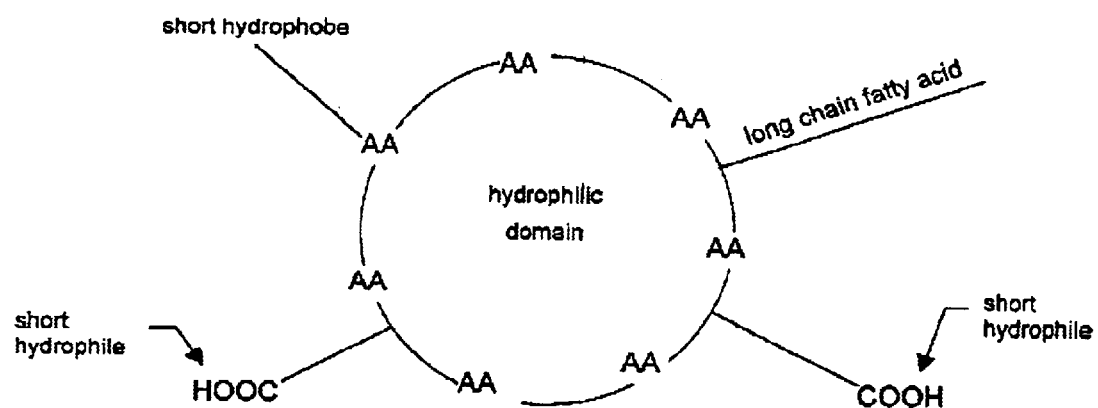
FIG. 2 is a schematic illustration of a surfactin molecule. "AA" represents an amino acid.

Another example of a compound meeting the requirements outlined above is a compound, or a group of structurally-related compounds, all known as surfactin. This material is naturally occurring, being produced by fermentation of certain strains of *Bacillus subtilis*, and is commercially available from Showa Denko, KK, Japan. The structure of the molecule is unusual, being composed of a large hydrophilic ring containing seven amino acids bonded to each other by six peptide bonds and an ester bond, and having on either side two short-chain hydrocarbons with free carboxyl groups carrying anionic charges, (the ring and carboxyl groups constituting the hydrophilic domain), with a hydrophobic domain comprising a long chain fatty acid residue. A schematic representation of this type of molecule is seen in FIG. 2. It will readily be seen that these molecules possess an asymmetrical arrangement of the hydrophilic and hydrophobic moieties, and also have the desired rigidity in the presence of the amino acid ring structure.

As a third example, and one in which there is not a single compound, is a combination of xanthan, polyglucomannan, a high HLB emulsifier, and a low HLB emulsifier. Such a combination is available from Uniqema as part of the Arlatone Versaflex Series of high performance emulsion stabilization systems.

The water-thin emulsions of the present invention have two distinct advantages over prior art water-thin emulsions. The first advantage is that the pseudoemulsifiers of this type are innately mild, being relatively non-water soluble, and hence, non-reactive with skin, and therefore are less irritating by nature than an ethoxylated emulsifiers. In addition, the compounds of these systems, even though not ordinarily effective as emulsifiers on their own, have proven to be unusually effective in stabilizing this type of emulsion, thereby improving even further the mildness of the emulsions by reducing the amount of emulsifier needed. The oil-in water emulsions of the invention ordinarily will contain no more than about 3% total pseudoemulsifer, preferably no more than 2% pseudoemulsifiers, and more preferably, no more than 0.5% pseudoemulsifier. Because of the unusual properties of these pseudoemulsifiers, the emulsion is stable even in the substantial absence of added emulsion stabilizers. It may, however, be desired to thicken slightly the water-thin emulsion depending on the desired nature of the final product. Therefore, it is possible to add to the emulsion a small amount of one or more cosmetic powders, not for stabilization, but merely to modify the viscosity of the product. Examples of types of powders that can be used in the present emulsion are silica powders, polymethylmethacrylate, bismuth oxychloride, boron nitride, barium sulfate, mica, sericite, muscovite, synthetic mica, titanium oxide coated mica, titanium oxide coated bismuth oxychloride, talc, polyethylene, nylon, polypropylene, acrylates/alkyl acrylates crosspolymer, acrylamide copolymers, and the like. The powders can be used in an amount of up to about 20%, but ordinarily the powders will be used in small amounts, generally no greater than about 5% of the total weight of the emulsion, more preferably no greater than 2%. In certain embodiments, the emulsion will contain less than 0.5% by weight of powders.

In order to prepare the water-thin emulsions of the invention, the pseudoemulsifier is combined with any standard oil and water emulsion components. The aqueous phase may be any cosmetically acceptable water based material, such as deionized water, or a floral water. The oil phase may be any cosmetically or pharmaceutically acceptable oil, such an oil being defined for the present purpose as any pharmaceutically or cosmetically acceptable material which is substantially insoluble in water. As the oils can perform different functions in the composition, the specific choice is dependent on the purpose for which it is intended. The oils may be volatile or non-volatile, or a mixture of both. For example, suitable volatile oils include, but are not limited to, both cyclic and linear silicones, such as octamethylcyclotetrasiloxane and decamethylcyclopentasiloxane; or straight or branched chain hydrocarbons having from 8–20 carbon atoms, such as decane, dodecane, tridecane, tetradecane, and C8–20 isoparaffins.

Non-volatile oils include, but are not limited to, vegetable oils, such as coconut oil, jojoba oil, corn oil, sunflower oil, palm oil, soybean oil; carboxylic acid esters such as isostearyl neopentanoate, cetyl octanoate, cetyl ricinoleate, octyl palmitate, dioctyl malate, coco-dicaprylate/caprate, decyl isostearate, myristyl myristate; animal oils such as lanolin and lanolin derivatives, tallow, mink oil or cholesterol; glyceryl esters, such as glyceryl stearate, glyceryl dioleate, glyceryl distearate, glyceryl linoleate, glyceryl myristate; non-volatile silicones, such as dimethicone, dimethiconol, dimethicone copolyol, phenyl trimethicone, methicone, simethicone; and nonvolatile hydrocarbons, such as isoparaffins, squalane, or petrolatum.

The ratio of oil phase:water phase in the emulsion is not critical, and can range from about 10:90 to about 50:50, but is more preferably from about 30:70 to about 40:60.

The pseudoemulsifier is ordinarily added to the phase in which it is soluble, or to either phase if it is not soluble in either, along with any active components which may be desired in the emulsion, and all components mixed together at low pressure. The mixture is then subjected to high pressure mixing. By "high pressure" in the present context is meant a pressure of at least about 15,000 psi, preferably at least about 25,000 psi, more preferably about 35,000 psi; generally, a single pass through the high pressure equipment is adequate to achieve an emulsion of the desired type at higher pressures, although at lower pressures, more than one pass may be required. The amount of pseudoemulsifier employed is preferably no more than 2%, more preferably no more than 1%. Amounts of as low as 0.25% can be employed, although about 0.5 to about 1% is generally preferred. It will be understood that the amount of pseudoemulsifier and level of pressure can be varied inversely, with a higher pressure treatment allowing the use of lower levels of emulsifier to produce a stable emulsion, while lower pressure treatments will ordinarily require a level of emulsifier at the higher end of the effective range. The particle size distribution is normally narrow, and very small, usually in the range of about,50–150 nm, preferably with an average size of about 50–100 nm, more preferably about 50 nm.

An oil-in-water emulsion so prepared can be used as such, or it can be further used as a base to which an additional water phase, particularly one enriched with active ingredients that may be too temperature sensitive to be added to the high-temperature pre-mix, can be added, under low pressure. This approach yields an oil-in-water emulsion in the form of either a spray, lotion or cream. In the preparation of such a composition, the oil-in-water emulsion can be added to the water in an amount ranging from about 90:10 emulsion:water to 10:90 emulsion:water.

If desired, the viscosity of the resulting products can be increased by the addition of water-soluble thickeners such as acrylates crosspolymers and copolymers, carbomer, guar gum, carageenan, cellulosics, mannan, sulfonic acid polymers, acrylamide copolymer, xanthan gum and the like. Preferably, the amount-of thickener ranges between about 0.01 to about 1%, preferably no more than about 0.5%.

In a particularly preferred embodiment, the water-thin emulsion is added to a water-in-oil emulsion, so as to prepare a multiple phase emulsion. This type of emulsion is valuable for a number of reasons. First, it provides a means for incorporating actives in the same vehicle which would not ordinarily be compatible in the same phase, by incorporating them in different phases. It also is a useful vehicle for delayed release of actives on and into the skin, by virtue of the necessity of passing through the multiple phases. Despite their clear value, however, such emulsions are not frequently employed, as the additional phase introduces further problems with stability, and therefore, they frequently require the use of large quantities of emulsifiers and/or emulsion stabilizers. It has now been found, unexpectedly, that the water-thin emulsion can provide a basis for the preparation of a multiple emulsion, serving as the outer water phase, without the need for large quantities of emulsifiers. In such preparation, the premade water-thin emulsion serves as the water phase, and is mixed, under normal, low-pressure conditions, with a premade standard water-in-oil emulsion. The two emulsions are preferably combined in a ratio of about 80 water-thin emulsion:20 water-in-oil emulsion up to 50:50 water-thin:water-in-oil, to yield a stable multiple emulsion. Surprisingly, these multiple emulsions can be prepared with no more than 2% emulsifiers, and preferably no more than about 1.5% emulsifiers total in the multiple emulsion.

Even more unexpectedly, the multiple emulsions can be prepared with an even number of phases, e.g., four phases, rather than the standard uneven number ordinarily found in multiple emulsions, such as water-in-oil-in-water. This is made possible by the small droplet size of the oils in the water-thin emulsion, which essentially presents itself as water to a standard emulsion, and is therefore readily incorporated without the addition of large amounts of emulsifiers.

Generally speaking, the multiple emulsion can be prepared with little or no "traditional" emulsifier, a traditional emulsifiers being one which, unlike the pseudoemulsifiers, are capable of stabilizing emulsions on their own, even at relatively low levels. When combined with a water-thin oil-in-water emulsion to make the multiple emulsion, the multiple emulsion may employ small amounts of a traditional oil-in-water emulsifier. Examples of useful oil-in-water emulsifers include, but are not limited to, sorbitol derivatives, such as sorbitan monolaurate and polysorbate 20; ethoxylated alcohols such as laureth-23, ethoxylated fatty acids such as PEG-1000 stearate; amidoamine derivatives such as stearamidoethyl diethylamine; sulfate esters such as sodium lauryl sulfate; phosphate esters such as DEA cetyl phosphate; fatty acid amine salts such as TEA stearate; and mixtures thereof. Additional examples can be found in McCutcheon's Emulsifiers and Detergents, 2000, the contents of which are incorporated herein by reference. If used, this type of emulsifier is incorporated in quantities of no more than about 2% by weight of the multiple emulsion, preferably no more than 1%, and more preferably, no more than about 0.5%. Stabilizers or thickeners, if used at all, can be employed as described for the water-thin emulsion alone.

The compositions of the invention can be used for any cosmetic or pharmaceutical purpose in which an standard or multiple emulsion is normally useful. For cosmetic purposes, the emulsions can be used in makeup products as well as skin-care products. In such cases, it may be desirable to incorporate into the emulsion additional components usually associated with the desired cosmetic uses, such as additional preservatives, fragrances, emollients, antiseptics, antiinflammatories, antibacterials, stabilizers, sunscreens, antioxidants, vitamins, pigments, dyes, humectants, and propellants, as well as other classes of materials the presence of which in the compositions may be cosmetically, medicinally, or otherwise desired. Such components can be found in the CTFA International Cosmetics Ingredients Dictionary, supra.

For pharmaceutical or therapeutic cosmetic use, the emulsion can incorporate any variety of topically applied therapeutic agents, particularly those that will benefit from adelayed release of active agents. Examples include, but are not limited to, agents for the eradication of age spots, keratoses and wrinkles, analgesics, anesthetics, anti-acne agents, antibacterials, antiyeast agents, antifungal agents, antiviral agents, antidandruff agents, antidermatitis agents, antipruritic agents, antiemetics, antimotion sickness agents, anti-inflammatory agents, antihyperkeratolytic agents, anti-dry skin agents, antiperspirants, antipsoriatic agents, antiseborrheic agents, hair conditioners and hair treatment agents, antiaging agents, antiwrinkle agents, antiasthmatic agents and bronchodilators, sunscreen agents, antihistamine agents, skin lightening agents, depigmenting agents, vitamins, corticosteroids, self-tanning agents, hormones, retinoids, such as retinoic acid, 13-cis retinoic acid, and retinol, topical cardiovascular agents, clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, hydroquinone, minocycline, naproxen, ibuprofen, theophylline, cromolyn, albuterol, topical steroids such as hydrocortisone, hydrocortisone 21-acetate, hydrocortisone 17-valerate, and hydrocortisone 17-butyrate, betamethasone valerate, betamethasone diprionate, triamcinolone acetonide, fluocinonide, clobetasol, proprionate, benzoyl peroxide, crotamiton, propranolol, promethazine, vitamin A palmitate, vitamin E acetate and mixtures thereof.

The invention is further illustrated by the following non-limiting examples.

EXAMPLES

Example 1

This example illustrates the preparation of an oil-in-water emulsion of the invention.

| Material | Weight % | | |
| --- | --- | --- | --- |
| | Batch 1 | Batch 2 | Batch 3 |
| Water Phase | | | |
| Deionized water | 65.25 | 64.70 | 62.50 |
| Disodium EDTA | 0.10 | 0.10 | 0.10 |
| Methyl paraben | 0.05 | 0.05 | 0.05 |
| Butylene glycol | 3.00 | 3.00 | 3.00 |
| phenoxyethanol | 0.40 | 0.40 | 0.40 |
| Oil Phase | | | |
| Behenyl alcohol | 0.75 | 0.75 | 0.75 |
| Pentaerythrityl tetraoctanoate | 30.00 | 30.00 | — |
| Stepan RM1 | 0.50 | 1.00 | 0.50 |
| C12–15 alkyl benzoate | — | — | 30.00 |

The water phase materials are heated to 85–90° C. The oil phase materials are heated to 85° C. The oil phase materials are added to the water phase materials using a Silverson (low pressure) homogenizer. The batch is then run through a DEE/BEE 2000 homogenizer at 40,000 psi, and cooled to room temperature in the machine.

Example 2

This example illustrates the use of the emulsions prepared above in creating a variety of low emulsifier skin care products.

A. Low Emulsifier Creme

| Material | Weight % |
| --- | --- |
| Phase I | |
| Deionized Water | 19.00 |
| acrylamide copolymer (1.5%) | 10.00 |
| Glycerine | 10.00 |
| antiinflammatory polysaccharide | 1.00 |
| Phase II | |
| Batch 3 | 39.60 |
| Acrylates/C10–30 alkyl acrylates Crosspolymer (2%) | 20.00 |
| triethanolamine | 0.40 |

Phase I and Phase II components are separately premixed by propeller mixing. The two phases are then mixed to homogeneity with a propeller or paddle.

B. Low Emulsifier Milk Lotions

| Material | Weight % | |
| --- | --- | --- |
| Batch 2 | 97.00 | 99.00 |
| Magnesium ascorbyl phosphate | 3.00 | — |
| N-acetyl glucosamine | — | 1.00 |

C. Low Emulsifier Cleanser

| Material | Weight % |
| --- | --- |
| Phase I | |
| Deionized water | 18.70 |
| methyl paraben | 0.10 |
| Phase II | |
| glycerine | 10.00 |
| Phase III | |
| Acrylamide copolymer (1.5%) | 10.00 |
| Phase IV | |
| Acrylates/C10–30 alkyl acrylates crosspolymer (2%) | 20.00 |
| Phase V | |
| Batch 2 | 39.60 |
| Phase VI | |
| triethanolamine | 0.40 |
| deionized water | 0.50 |
| Phase VII | |
| Germall 115 | 0.20 |
| deionized water | 0.50 |

Phase I materials are heated to 75° C., and cooled to room temperature. Phases II, III, and IV are added to Phase I under propeller agitation. After addition of Phase IV, viscosity increases, requiring a change to a paddle. Phases V, VI and VII are then added to the mixture, and mixed to homogeneity.

Example 3

This example illustrates the process of preparing a multiple emulsion according to the invention.

A. A Water-in-oil Phase is Prepared as Follows:

| Material | Weight % |
| --- | --- |
| Phase I | |
| Cyclomethicone/dimethicone | 5.00 |
| Phenyltrimethicone | 5.00 |
| Dimethicone/copolyol crosspolymer | 7.00 |
| Cyclomethicone | 1.00 |
| Dimethicone | 8.00 |
| Phase II | |
| Xanthan gum | 0.20 |
| Deionized water | 64.30 |
| Sodium chloride | 1.00 |
| Butylene glycol | 5.00 |
| Parabens | 0.50 |

The oil phase ingredients are combined together, and the water phase ingredients are combined together. The water phase is then slowly added to the oil phase, and homogenized until uniform.

B. Water-thin Low Emulsifier Emulsion

| Material | Weight % |
| --- | --- |
| Phase I | |
| deionized water | 32.50 |
| Arlatone Versaflex High Performance Emulsion Stabilizer* | 1.00 |
| Phase II | |
| Deionized water | 32.05 |
| Methyl paraben | 0.20 |
| Butylene glycol | 3.00 |
| Phenoxyethanol | 0.40 |
| Phase III | |
| Behenyl alcohol | 0.75 |
| Pentaerythrityl-tetraethylhexanoate | 30.00 |
| Beta-carotene | 0.10 |

*Uniqema

In Phase I, the emulsifier is added to water at 80° C. Phase II ingredients are added to Phase I at 80° C. Phase III ingredients are combined and then homomixed with Phase I and II ingredients at greater than 10,000 rpm for 5 minutes. The combined components are then passed through a microfluidizer at 16,000 psi three times to achieve a water-thin emulsion.

C. Multiple Emulsion

| Material | Weight % |
| --- | --- |
| Polysorbate 20 | 0.20 |
| Carbopol | 1.00 |
| O/W emulsion from B. | 78.80 |
| W/O emulsion from A. | 20.00 |

The O/W emulsion is combined with the Carbopol using static mixing. Polysorbate 20 is then added. The W/O emulsion is slowly added to the O/W phase utilizing static mixing. When the addition is complete, the mixing is continued for about 5 minutes until the multiple emulsion is uniform.

Similar positive results are obtained in preparing a multiple emulsion as described above, utilizing RM1 as the pseudoemulsifier, and combining the O/W emulsion and the W/O emulsion in a ratio of 60:40.

What is claimed is:

1. A multiple emulsion incorporating a water-thin oil-in-water emulsion comprising a non-phospholipid, non-ethoxylated pseudoemulsifier system, the system having a chemical composition of one or more compounds with at least two hydrophobic moieties, at least two polar moieties, or at least two of both hydrophobic and polar moieties, the size, shape and/or planar arrangement of the hydrophobic and polar moieties being asymmetrical with respect to each other, each polar moiety being of a different size or shape than the other polar moiety if present, and each hydrophobic moiety being of different size or shape than the other if present.

2. The emulsion of claim 1 in which the hydrophobic moieties are of different chain lengths.

3. The emulsion of claim 1 in which at least one of the moieties has a closed ring structure.

4. The emulsion of claim 1 in which at least one of the moieties is a long straight-chain moiety.

5. The emulsion of claim 1 in which at least one of the moieties has a closed ring structure, and one of the moieties is a long, straight chain moiety.

6. The emulsion of claim 5 in which the system comprises a hydrophobic closed ring structure, and a long chain hydrophobe, separated from each other by a hydrophilic moiety.

7. The emulsion of claim 6 in which the hydrophilic moiety is selected from the group consisting of hydroxyl, amide, ester, or carboxyl moieties, hydrocarbons chains substituted with hydroxyl, amide, ester, or carboxyl moieties, and combinations thereof.

8. The emulsion of claim 5 in which the system comprises a hydrophilic closed ring structure, at least one carboxyl moiety, and a long chain fatty acid moiety.

9. The emulsion of claim 1 in which the pseudoemulsifier system comprises more than one compound.

10. The emulsion of claim 9 in which at least one of the compounds comprises a long, straight-chain hydrocarbon moiety.

11. The emulsion of claim 10 in which at least one of the compounds comprises a hydrophilic moiety selected from the group consisting of hydroxyl, amide, ester, or carboxyl moieties, hydrocarbons chains substituted with hydroxyl, amide, ester, or carboxyl moieties, and combinations thereof.

12. The emulsion of claim 11 in which the system further comprises a polymer selected from the group consisting of disaccharides, polysaccharides, and predominantly hydrophilic proteins or peptides.

13. The emulsion of claim 9 that comprises no greater than 1% of traditional emulsifier.

14. The emulsion of claim 1 that comprises no greater than 1% of traditional emulsifier.

15. A multiple emulsion prepared by combining a water-in-oil emulsion with the emulsion of claim 1, and mixing to substantial homogeneity.

16. A multiple emulsion incorporating a water-thin emulsion comprising a non-phospholipid, non-ethoxylated pseudoemulsifier system, the system having a chemical composition with at least one hydrophobic moiety and at least one polar moiety, the size, shape and/or planar arrangement of the hydrophobic and polar moieties being asymmetrical with respect to each other, in which the pseudoemulsifier is a 2-amidocarbonyl-benzoic acid compound having the formula (I)

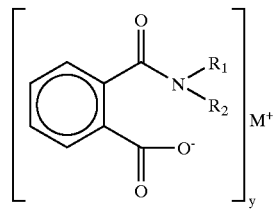

wherein $R_1$ and $R_1$ are independently H or $(CH2)nCH3$, wherein n=8–22, provided that at least one of $R_1$ and $R_2$ is H, wherein $M^+$ is a cation selected from the group consisting of H, Na, K, NH4, basic amino acids, Ba, Ca, Mg, Al, Ti, and Zr, and y is an integer of a value satisfying the valency of $M^+$.

17. The emulsion of claim 16 that comprises no greater than 1% of traditional emulsifier.

18. A multiple emulsion comprising a water-thin emulsion comprising a non-phospholipid, non-ethoxylated pseudoemulsifier system, the system having a chemical composition with at least one hydrophobic moiety and at least one polar moiety, the size, shape and/or planar arrangement of the hydrophobic and polar moieties being asymmetrical with respect to each other, in which the pseudoemulsifier is surfactin.

19. The emulsion of claim 18 that comprises no greater than 1% of traditional emulsifier.

* * * * *